(12) United States Patent
Ogami et al.

(10) Patent No.: US 12,138,340 B2
(45) Date of Patent: Nov. 12, 2024

(54) COMPOSITION COMPRISING PIGMENT COATED WITH ISOPROPYL TITANIUM TRIISOSTEARATE

(71) Applicant: L'OREAL, Paris (FR)

(72) Inventors: Kazunori Ogami, Kawasaki (JP); Mariko Okamoto, Kawasaki (JP)

(73) Assignee: L'OREAL, Paris (FR)

( * ) Notice: Subject to any disclaimer, the term of this patent is extended or adjusted under 35 U.S.C. 154(b) by 81 days.

(21) Appl. No.: 17/997,591

(22) PCT Filed: Jun. 25, 2021

(86) PCT No.: PCT/JP2021/025054
§ 371 (c)(1),
(2) Date: Oct. 31, 2022

(87) PCT Pub. No.: WO2022/004865
PCT Pub. Date: Jan. 6, 2022

(65) Prior Publication Data
US 2023/0225958 A1    Jul. 20, 2023

(30) Foreign Application Priority Data
Jun. 29, 2020  (JP) .................................. 2020-111555
Aug. 26, 2020  (FR) ........................................ 2008718

(51) Int. Cl.
| | | |
|---|---|---|
| A61Q 5/10 | (2006.01) |
| A61K 8/06 | (2006.01) |
| A61K 8/29 | (2006.01) |
| A61K 8/73 | (2006.01) |
| A61K 8/92 | (2006.01) |
| A61Q 5/06 | (2006.01) |

(52) U.S. Cl.
CPC ............... *A61K 8/92* (2013.01); *A61K 8/064* (2013.01); *A61K 8/29* (2013.01); *A61K 8/73* (2013.01); *A61Q 5/065* (2013.01); *A61Q 5/10* (2013.01); *A61K 2800/43* (2013.01)

(58) Field of Classification Search
CPC . A61K 8/92; A61K 8/064; A61K 8/29; A61K 8/73; A61K 2800/43; A61K 2800/48; A61K 2800/622; A61K 8/604; A61K 8/58; A61K 8/732; A61Q 5/065; A61Q 5/10; A61Q 17/04; A61Q 1/02
USPC ......................................................... 8/637.1
See application file for complete search history.

(56) References Cited

U.S. PATENT DOCUMENTS

| | | | |
|---|---|---|---|
| 5,840,883 A | 11/1998 | Suzuki et al. | |
| 5,843,417 A * | 12/1998 | Hanna ...................... | A61Q 1/02 514/844 |
| 5,942,213 A * | 8/1999 | Bara ...................... | A61K 8/064 424/78.03 |
| 2010/0112019 A1* | 5/2010 | Thevenet ................. | A61K 8/19 424/78.02 |
| 2011/0070177 A1* | 3/2011 | Arnaud ..................... | A61K 8/06 206/581 |
| 2011/0150801 A1* | 6/2011 | Lebre-Lemonnier ....................... | A61K 8/064 424/63 |
| 2015/0157539 A1* | 6/2015 | Shimizu ............... | A61K 8/8152 424/59 |
| 2015/0290090 A1* | 10/2015 | Matsufuji .............. | A61Q 17/04 424/59 |
| 2017/0281479 A1* | 10/2017 | Arnaud ................... | A61K 8/894 |
| 2018/0110686 A1* | 4/2018 | Luan ...................... | A61K 8/375 |
| 2018/0369083 A1* | 12/2018 | Valverde .................. | A61K 8/37 |

FOREIGN PATENT DOCUMENTS

| | | | | |
|---|---|---|---|---|
| CN | 108324595 A | 7/2018 | | |
| CN | 108366917 A | 8/2018 | | |
| CN | 108472206 A | 8/2018 | | |
| CN | 108601716 A * | 9/2018 | ............... | A61K 8/29 |
| CN | 108601722 A | 9/2018 | | |
| EP | 0856305 A2 | 8/1998 | | |
| EP | 2319483 A1 | 5/2011 | | |
| FR | 2686510 A1 | 7/1993 | | |
| FR | 3082745 A1 | 12/2019 | | |
| WO | 2017101106 A1 | 6/2017 | | |
| WO | 2019/243613 A1 | 12/2019 | | |
| WO | 2020/013182 A1 | 1/2020 | | |

OTHER PUBLICATIONS

Office Action dated Nov. 22, 2023 for the corresponding Chinese Patent Application No. 202180035204.7, with English translation, 21 pages.
Wang Yuhan, "Scientific Common Sense of Family Life", Standards Press of China, Jan. 31, 1991, p. 367 (the English translation(s) of the Office Action(s) is/are (a) concise explanation(s) of the relevance.).
International Search Report for the corresponding patent application No. PCT/JP2021/025054 dated Nov. 2, 2021.
Office Action dated Sep. 19, 2023, for the corresponding Japanese Patent Application No. 2023-512811, with English translation.
Office Action dated Jun. 15, 2023 for the corresponding Chinese patent application No. 202180035204.7, with English translation.
Li Anping et al., "Principles and Safe Use of Food Additives", p. 232, Sep. 30, 2011 (the English translation of the Office Action is a concise explanation of the relevance).

(Continued)

*Primary Examiner* — Eisa B Elhilo
(74) *Attorney, Agent, or Firm* — LUCAS & MERCANTI, LLP

(57) ABSTRACT

The present invention relates to a composition in the form of a water-in-oil (W/O) emulsion comprising an oily phase and an aqueous phase, comprising: (a) at least one oil; (b) at least one organic lipophilic gelling agent; (c) at least one pigment coated with isopropyl titanium triisostearate; and (d) water; wherein the amount of the (b) lipophilic gelling agent is greater than 0% by weight and less than 5% by weight relative to the total weight of the composition, and the amount of the aqueous phase is at least 50% by weight relative to the total weight of the composition.

14 Claims, No Drawings

(56) References Cited

OTHER PUBLICATIONS

Liu Wen, China Press of Traditional Chinese Medicine, "Medicinal Polymer Materials, National Traditional Chinese Medicine Industry Higher Education Textbook for the "13th Five-Year Plan"", pp. 117-118, Jun. 3, 2017 (the English translation of the Office Action is a concise explanation of the relevance).

"KSG 210® technical data sheet", Shin-Etsu Chemical Co., Ltd , https://www.shinetsusiliconeglobal.com/products/personalcare/pdf/KSG/KSG-210.pdf , pp. 1-2 , published: Nov. 7, 2017.

Office Action dated Apr. 9, 2024 for the corresponding Chinese Patent Application No. 202180035204.7, with English translation, 33 pages.

\* cited by examiner

COMPOSITION COMPRISING PIGMENT COATED WITH ISOPROPYL TITANIUM TRIISOSTEARATE

CROSS REFERENCE TO RELATED APPLICATION

This application is a 371 of PCT/JP2021/025054 filed on Jun. 25, 2021 which, in turn, claimed the priority of Japanese Patent Application No. 2020-111555 filed on Jun. 29, 2020 and French Patent Application No. 2008718 filed on Aug. 26, 2020, all of which are incorporated herein by reference.

TECHNICAL FIELD

The present invention relates to a composition comprising at least one pigment coated with isopropyl titanium triisostearate, in particular, a composition in the form of a water-in-oil (W/O) emulsion, for a keratin substance such as skin.

BACKGROUND ART

Foundations are known and used in the cosmetic field to impart even color to keratinous substances such as skin. Emulsions are commonly employed as the form of liquid foundation products since they are pleasant to use due to the feeling of freshness and the moisture that the aqueous phase can provide. Also, a good coverage property as well as stability are required in liquid foundation products.

DISCLOSURE OF INVENTION

An objective of the present invention is to provide a composition in the form of a water-in-oil (W/O) emulsion for a keratin substance, such as skin, which has an improved coverage property and stability and can provide a fresh feeling to the keratinous substance.

The above objective of the present invention can be achieved by a composition in the form of a water-in-oil (W/O) emulsion comprising an aqueous phase and an oily phase, comprising:
   (a) at least one oil;
   (b) at least one organic lipophilic gelling agent;
   (c) at least one pigment coated with isopropyl titanium triisostearate; and
   (d) water;
   wherein
   the amount of the (b) organic lipophilic gelling agent is greater than 0% by weight and less than 5% by weight relative to the total weight of the composition, and
   the amount of the aqueous phase is at least 50% by weight relative to the total weight of the composition.

The (b) organic lipophilic gelling agent may be chosen from polysaccharide fatty acid esters, semi-crystalline polymers, polyamides, and mixtures thereof.

The (b) organic lipophilic gelling agent may be chosen from polysaccharide fatty acid esters.

The polysaccharide fatty acid esters may be dextrin esters.

The pigment of the (c) pigment coated with isopropyl titanium triisostearate may be chosen from metal oxides, preferably titanium dioxide, iron oxides, and mixtures thereof.

The amount of the (c) pigment(s) coated with isopropyl titanium triisostearate may be 0.1% by weight or more, preferably 1% by weight or more, more preferably 2% by weight or more, and most preferably 4% by weight or more, and may be 20% by weight or less, preferably 15% by weight or less, more preferably 10% by weight or less, and most preferably 8% by weight or less, relative to the total weight of the composition.

The amount of the aqueous phase may be 90% by weight or less, preferably 80% by weight or less, more preferably 70% by weight or less, and even more preferably 60% by weight or less, relative to the total weight of the composition.

The amount of the (a) oil may be 5% by weight or more, preferably 10% by weight or more, more preferably 15% by weight or more, and most preferably 20% by weight or more, and may be 45% by weight or less, preferably 40% by weight or less, more preferably 35% by weight or less, and most preferably 30% by weight or less, relative to the total weight of the composition.

The amount of the (d) water may be 20% by weight or more, preferably 30% by weight or more, more preferably 32% by weight or more, and even more preferably 35% by weight or more, and may be 70% by weight or less, preferably 60% by weight or less, more preferably 50% by weight or less, and even more preferably 45% by weight or less, relative to the total weight of the composition.

The composition according to the present invention may further include at least one hydrophilic gelling agent.

The composition according to the present invention may further include at least one organic UV filter.

The amount of the oil phase may be 5% by weight or more, preferably 10% by weight or more, more preferably 20% by weight or more, and even more preferably 30% by weight or more, and may be 49% by weight or less, preferably 45% by weight or less, relative to the total weight of the composition.

The present invention also relates to a cosmetic process for a keratin substance such as skin, comprising the step of applying onto the keratin substance the composition according to the present invention.

The present invention also relates to a composition in the form of a water-in-oil (W/O) emulsion comprising an oily phase and an aqueous phase, comprising:
   (a) at least one oil;
   (b) at least one organic lipophilic gelling agent;
   (c) at least one pigment coated with isopropyl titanium triisostearate;
   (d) water; and
   (e) at least one hydrophilic gelling agent selected from glycosaminoglycans and their salts, and their derivatives, preferably hyaluronic acid and their salts, and their derivatives, such as sodium hyaluronate and acetylated sodium hyaluronate, and mixtures thereof,
   wherein
   the amount of the (b) lipophilic gelling agent is greater than 0% by weight and less than 5% by weight relative to the total weight of the composition, and
   the amount of the aqueous phase is at least 50% by weight relative to the total weight of the composition.

In this embodiment, the (b) organic lipophilic gelling agent may be dextrin esters.

BEST MODE FOR CARRYING OUT THE INVENTION

After diligent research, the inventors have discovered that a W/O emulsion composition comprising at least 50% by weight of an aqueous phase and a combination of a specific amount of at least one organic lipophilic gelling agent and at least one pigment coated with isopropyl titanium triisostearate can provide keratinous substances, such as skin, with an improved fresh feeling as well as a coverage effect, while it remains stable.

Thus, the composition, preferably a cosmetic composition for a keratin substance, such as skin, according to the present invention is in the form of a W/O emulsion comprising an aqueous phase and an oily phase, and comprises:
- (a) at least one oil;
- (b) at least one organic lipophilic gelling agent;
- (c) at least one pigment coated with isopropyl titanium triisostearate; and
- (d) water;

wherein the amount of the (b) organic lipophilic gelling agent is greater than 0% by weight and less than 5% by weight relative to the total weight of the composition, and the amount of the aqueous phase is at least 50% by weight relative to the total weight of the composition.

Hereafter, the composition according to the present invention will be described in a detailed manner.

[Composition]

The composition of the present invention is in the form of a W/O emulsion comprising an aqueous phase and an oily phase.

The composition may be a cosmetic composition, preferably a cosmetic composition for a keratin substance, and more preferably a skin care cosmetic composition. Preferably, the composition according to the present invention can be used as a liquid foundation, a make-up base, and a skin care cream composition, and in particular a liquid foundation. The composition can be in the form of a lotion, a milky lotion, a cream, a liquid gel, a paste, or a serum.

The amount of the aqueous phase is at least 50% by weight relative to the total weight of the composition. The amount of the aqueous phase may be 90% by weight or less, preferably 80% by weight or less, more preferably 70% by weight or less, and even more preferably 60% by weight or less, relative to the total weight of the composition.

The amount of the oil phase is not particularly limited. In general, the amount of the oil phase may be 5% by weight or more, preferably 10% by weight or more, more preferably 20% by weight or more, and even more preferably 30% by weight or more, and may be 49% by weight or less, preferably 45% by weight or less, relative to the total weight of the composition. The oil phase can include lipophilic, liposoluble or lipodispersible ingredients.

The composition according to the present invention comprises (a) at least one oil, (b) at least one organic lipophilic gelling agent, (c) at least one pigment coated with isopropyl titanium triisostearate, and (d) water. The ingredients in the composition will be described in a detailed manner below.

(Oil)

The composition according to the present invention comprises (a) at least one oil. Two or more (a) oils may be used in combination. Thus, a single type of oil or a combination of different types of oil may be used. The (a) oil forms the oily phase in the composition according to the present invention.

As used herein, the expression "oil" means a fatty compound or substance which is in the form of a liquid or a paste (non-solid) at room temperature (25° C.) under atmospheric pressure (760 mmHg). These oil(s) may be volatile or non-volatile, preferably non-volatile.

The (a) oil may be a non-polar oil such as a hydrocarbon oil, a silicone oil, or the like; a polar oil such as a plant or animal oil and an ester oil or an ether oil; or a mixture thereof.

It is preferable that the (a) oil be selected from the group consisting of oils of plant or animal origin, synthetic oils, silicone oils, and hydrocarbon oils, and mixtures thereof.

As examples of plant oils, mention may be made of, for example, linseed oil, camellia oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

The esters according to this variant may also be selected from monoesters, diesters, triesters, tetraesters and polyesters, and mixtures thereof.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, cetyl ethylhexanoate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

As examples of artificial triglycerides, mention may be made of, for example, capryl caprylic triglycerides, glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

As examples of preferable ester oils, mention may be made of, for example, diisopropyl adipate, dioctyl adipate, 2-ethylhexyl hexanoate, ethyl laurate, cetyl octanoate, cetyl ethylhexanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrityl tetra(2-ethylhexanoate), 2-ethylhexyl succinate, diethyl sebacate, and mixtures thereof.

As examples of silicone oils, mention may be made of, for example, linear organopolysiloxanes such as alkyldimethicone, in particular dimethylpolysiloxane and methylhydrogenpolysiloxane; phenylmethicone, such as diphenylsiloxy phenyl trimethicone; and cyclic organopolysiloxanes such as cyclohexasiloxane, octamethylcyclotetrasiloxane, decamethylcyclopentasiloxane, dodecamethylcyclohexasiloxane, and the like; and mixtures thereof. Preferably, the silicone oil is chosen from liquid polydialkylsiloxanes, especially liquid polydimethylsiloxanes (PDMS, dimethicone) and liquid polyorganosiloxanes comprising at least one aryl group. These silicone oils may also be organomodified. The organomodified silicones that can be used in accordance with the present invention are silicone oils as defined above and comprise in their structure one or more organofunctional groups attached via a hydrocarbon-based group.

Hydrocarbon oils may be chosen from:
  linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane; and
  linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosane, and decene/butene copolymer; and mixtures thereof.

It may be preferable that the (a) oil be chosen from non-polar hydrocarbon oils which are in the form of a liquid at a room temperature.

It is also preferable that the (a) oil be selected from the group consisting of hydrocarbon oils, esters of $C_4$-$C_{22}$ dicarboxylic or tricarboxylic acids and of $C_1$-$C_{22}$ alcohols, and esters of $C_4$-$C_{22}$ monocarboxylic, dicarboxylic or tricarboxylic acids and of non-sugar $C_4$-$C_{26}$ dihydroxy, $C_4$-$C_{15}$ trihydroxy, tetrahydroxy or pentahydroxy alcohols, and mixtures thereof.

The (a) oil(s) may be present in an amount of 5% by weight or more, preferably 10% by weight or more, more preferably 15% by weight or more, and most preferably 20% by weight or more, and may be present in an amount of 45% by weight or less, preferably 40% by weight or less, more preferably 35% by weight or less, and most preferably 30% by weight or less, relative to the total weight of the composition.

(Organic Lipophilic Gelling Agent)

The composition according to the present invention comprises (b) at least one organic lipophilic gelling agent. Two or more (b) organic lipophilic gelling agents may be used in combination. Thus, a single type of organic lipophilic gelling agent or a combination of different types of organic lipophilic gelling agents may be used.

The organic lipophilic gelling agent of the present invention is liposoluble or lipodispersible.

For the purposes of the present invention, the term "lipophilic" here can mean substances having a solubility of at least 1 g/L, preferably at least 10 g/L, and more preferably at least 100 g/L, in an oil at room temperature (25° C.) and atmospheric pressure (105 Pa). In another aspect, the term "lipophilic" can refer to substances which are not soluble in water or which have a solubility of 1 g/L or less, or 0.1 g/L or less in water, at 25° C. and atmospheric pressure.

For the purposes of the present invention, the term "lipophilic gelling agent" means a compound that is capable of gelling the oily phase of the compositions according to the present invention. The gelling agent is lipophilic and can thus be present in the oily phase of the composition.

The organic lipophilic gelling agent is advantageously chosen from polysaccharide fatty acid esters, semi-crystalline polymers, polyamides, and mixtures thereof.

Polysaccharide Fatty Acid Ester

The polysaccharides in the polysaccharide fatty acid ester include, but are not limited to, dextrin and inulin. Preferably, the polysaccharide fatty acid esters are dextrin esters.

The fatty acids in the polysaccharide fatty acid ester include, but are not limited to, linear or branched, saturated or unsaturated $C_{10}$-$C_{24}$, preferably $C_{12}$-$C_{20}$ fatty acids, for example, myristic acid, oleic acid, palmitic acid, stearic acid, isopalmitic acid, and isostearic acid.

Preferably, the polysaccharide fatty acid ester is selected from dextrin myristate and/or dextrin palmitate, and mixtures thereof.

According to a preferred embodiment, the dextrin ester is dextrin palmitate. This product may be chosen, for example, from those sold under the names Rheopearl TL®, Rheopearl KL® and Rheopearl® KL2 by the company Chiba Flour Milling.

Semi-Crystalline Polymer

The term "semi-crystalline polymer" is understood to mean, within the meaning of the present invention, polymers comprising a crystallizable portion, pendent chain or block in the backbone, and an amorphous portion in the backbone and exhibiting a first-order reversible phase change temperature, in particular, a melting point (solid-liquid transition). When the crystallizable portion is a block of the polymer backbone, this crystallizable block has a chemical nature different from that of the amorphous blocks; in this case, the semi-crystalline polymer is a block polymer, for example, of the diblock, triblock or multiblock type.

The melting point of the semi-crystalline polymer is preferably less than 150° C.

The melting point of the semi-crystalline polymer is preferably greater than or equal to 30° C. and less than 100° C. More preferably, the melting point of the semi-crystalline polymer is greater than or equal to 30° C. and less than 70° C. The melting point can be measured in particular by any known method and especially with a differential scanning calorimeter (DSC).

Advantageously, the semi-crystalline polymer(s) of the composition of the present invention have a number-average molecular mass Mn of greater than or equal to 2,000, for example ranging from 2,000 to 800,000, preferably from 3,000 to 500,000, for example from 4,000 to 150,000 and better still from 4,000 to 99,000.

In the composition according to the present invention, the semi-crystalline polymers are advantageously soluble in the oily phase, to at least 1% by weight, at a temperature greater than their melting point. Apart from the crystallizable chains or blocks, the blocks of the polymers are amorphous. Within the meaning of the present invention, the expression "crystallizable chain or block" is understood to mean a chain or block which, if it were alone, would change from the amorphous state to the crystalline state reversibly, according to whether the temperature is above or below the melting point. Within the meaning of the present invention, a "chain" is a group of atoms, which is pendent or lateral with respect to the backbone of the polymer. A "block" is a group of atoms belonging to the backbone, which group constitutes one of the repeat units of the polymer.

Preferably, the crystallizable blocks or chains of the semi-crystalline polymers represent at least 30% of the total weight of each polymer and better still at least 40%. The semi-crystalline polymers having crystallizable blocks used according to the present invention are block or multiblock polymers. They can be obtained by polymerization of monomers comprising reactive double bonds (or ethylenic bonds) or by polycondensation. When the polymers of the present invention are polymers having crystallizable side chains, they are advantageously in random or statistical form.

The semi-crystalline polymers of the present invention are of synthetic origin. Moreover, they do not comprise a polysaccharide backbone.

The semi-crystalline polymers which can be used in the present invention are preferably chosen from polymers (homopolymers or copolymers) carrying at least one crystallizable side chain and polymers (homopolymers or copolymers) carrying in the backbone at least one crystallizable block. The crystallizable side chain(s) or block(s) are hydrophobic.

According to a specific embodiment of the present invention, the semi-crystalline polymers are chosen in particular from homopolymers and copolymers resulting from the polymerization of at least one monomer having a crystallizable chain(s), this chain being chosen from alkyl chains comprising at least 11 carbon atoms and at most 40 carbon atoms and better still at most 24 carbon atoms. They are in particular alkyl chains comprising at least 12 carbon atoms and they are preferably alkyl chains comprising from 14 to 24 carbon atoms ($C_{14}$-$C_{24}$). They can be hydrocarbon alkyl chains (carbon and hydrogen atoms) or fluoroalkyl or perfluoroalkyl chains (carbon atoms, fluorine atoms and possibly hydrogen atoms). When they are fluoroalkyl or perfluoroalkyl chains, they comprise at least 11 carbon atoms, at least 6 carbon atoms of which are fluorinated.

According to a specific embodiment of the present invention, the semi-crystalline polymer is chosen from homopolymers obtained by polymerization of at least one monomer having a crystallizable chain, chosen from $C_{14}$-$C_{24}$ alkyl (meth)acrylates, $C_{11}$-$C_{15}$ perfluoroalkyl (meth)acrylates, N—($C_{14}$ to $C_{24}$ alkyl)(meth)acrylamides with or without fluorine atoms, vinyl esters having $C_{14}$ to $C_{24}$ alkyl or perfluoroalkyl chains, vinyl ethers having $C_{14}$ to $C_{24}$ alkyl or perfluoroalkyl chains, $C_{14}$ to $C_{24}$ α-olefins or para-alkylstyrenes with a $C_{14}$ to $C_{24}$ alkyl group, and from the copolymers of these monomers obtained by copolymerization of these monomers with a hydrophilic monomer, preferably other than methacrylic acid, such as, for example, N-vinylpyrrolidone, hydroxyethyl acrylate, hydroxyethyl methacrylate or acrylic acid. Such copolymers can, for example, be copolymers of $C_{14}$-$C_{24}$-alkyl acrylate, $C_{14}$-$C_{24}$-alkyl methacrylate, $C_{14}$-$C_{24}$-alkylacrylamide or $C_{14}$-$C_{24}$-alkylmethacrylamide with N-vinylpyrrolidone, hydroxyethyl acrylate, hydroxyethyl methacrylate or acrylic acid, or their mixtures.

According to a specific embodiment of the present invention, the semi-crystalline polymer is a homopolymer resulting from the polymerization of a monomer having a crystallizable chain chosen from $C_{14}$-$C_{24}$ alkyl acrylates and $C_{14}$-$C_{24}$ alkyl methacrylates. Mention may in particular be made of those sold under the name Intelimer® by Landec, described in the brochure Intelimer® Polymers, Landec IP22. These polymers are in the solid form at ambient temperature. They carry crystallizable side chains and correspond to saturated $C_{14}$-$C_{24}$ alkyl acrylate or methacrylate homopolymers. Mention may more particularly be made of the stearyl acrylate homopolymer (Intelimer IPA-13.1) (INCI name: Poly C10-30 alkyl acrylate) or the behenyl acrylate homopolymer (Intelimer IPA-13.6) (INCI name: Poly C10-30 alkyl acrylate).

According to another specific embodiment of the present invention, the semi-crystalline polymer is a copolymer of $C_{14}$-$C_{24}$ alkyl acrylates or of $C_{14}$-$C_{24}$ alkyl methacrylates with acrylic acid. Mention may be made, as copolymers of this type, of the copolymers obtained by the copolymerization of behenyl acrylate and acrylic acid and the copolymers obtained by the copolymerization of stearyl acrylate and acrylic acid.

According to a preferred embodiment of the present invention, the semi-crystalline polymer is a homopolymer and it is chosen from the stearyl acrylate homopolymer (Intelimer IPA-13.1) (INCI name: Poly C10-30 alkyl acrylate), the behenyl acrylate homopolymer (Intelimer IPA-13.6) (INCI name: Poly C10-30 alkyl acrylate), and their mixtures.

Polyamide

For the purposes of the present invention, the term "polyamide" means a compound containing at least 2 amide repeating units, preferably at least 3 amide repeating units and better still 10 amide repeating units.

Polyamides as the lipophilic gelling agent are chosen from hydrocarbon-based polyamides and silicone polyamides, and mixtures thereof.

The term "hydrocarbon-based polyamide" means a polyamide formed essentially of, indeed even consisting of, carbon and hydrogen atoms, and optionally of oxygen or nitrogen atoms, and not comprising any silicon or fluorine atoms. It may contain alcohol, ester, ether, carboxylic acid, amine and/or amide groups.

Advantageously, the polyamide of the composition according to the present invention has a weight-average molecular mass of less than 100,000 g/mol (especially ranging from 1,000 to 100,000 g/mol), in particular less than 50,000 g/mol (especially ranging from 1,000 to 50,000 g/mol) and more particularly ranging from 1,000 to 30,000 g/mol, preferably from 2,000 to 20,000 g/mol and better still from 2,000 to 10,000 g/mol.

The hydrocarbon-based polyamide used in the present invention includes aliphatic polyamides, for example polyamide-4, polyamide-6, polyamide-8, polyamide-11, polyamide-12, polyamide-4,6, polyamide-6,6, polyamide-6, 9, polyamide-6,10, and polyamide-6,12; polyamides derived from an aliphatic diamine and an aromatic dicarboxylic acid, for example polyamide-4,T, polyamide-6,T, polyamide-4,I, etc., in which T stands for terephthalate and I stands for isophthalate; copolyamides of linear polyamides and copolyamides of an aliphatic and a partially aromatic polyamide, for example, 6/6,T, 6/6,6/6,T, as well as amorphous polyamides of the Trogamid® PA 6-3-T and Grilamid® TR 55 types.

Preferably, the hydrocarbon-based polyamides are selected from aliphatic polyamides, such as polyamide-4, polyamide-6, polyamide-8, polyamide-11, polyamide-12, polyamide-4,6, polyamide-6,6, polyamide-6, 9, polyamide-6,10, and polyamide-6,12.

Preferably, the hydrocarbon-based polyamides may be aliphatic polyamides containing dimer acid(s). The dimer acid included in the aliphatic polyamides is preferably a dimer of fatty acids, preferably linear or branched, saturated or unsaturated $C_6$-$C_{30}$ fatty acids, which are optionally substituted with one or more hydroxyl groups. More preferably, the dimer acid is a dimer of unsubstituted, linear, and saturated $C_6$-$C_{30}$ fatty acids, such as hydrogenated linoleic acids.

In a preferable embodiment of the present invention, the polyamide is an aliphatic polyamide terminated with (a) a monovalent acid(s) and/or (a) monovalent alcohol(s). The monovalent acid may be a monovalent fatty acid, preferably linear or branched, saturated or unsaturated $C_6$-$C_{30}$ fatty acids, which are optionally substituted with one or more hydroxyl groups. The monovalent alcohol may be a monovalent fatty alcohol, preferably nonoxyalkylenated, saturated or unsaturated, linear or branched, $C_6$ to $C_{30}$ fatty alcohol. More preferably, the monovalent alcohol may be nonoxyalkylenated, saturated, and linear $C_6$ to $C_{30}$ fatty alcohol, such as stearyl alcohol.

Preferentially, the polyamide is an aliphatic polyamide terminated with a monovalent alcohol.

According to a specific embodiment of the present invention, the polyamide is a polyamide comprising an amide ester terminator of formula (I):

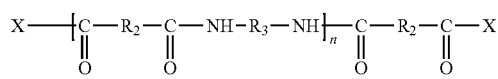

(I)

in which X represents an —$OR_1$ group in which $R_1$ is a linear or branched $C_8$ to $C_{22}$, preferably $C_{16}$ to $C_{22}$, alkyl radical which can be identical or different, $R_2$ is a $C_{28}$-$C_{42}$ dimer diacid residue, $R_3$ is an ethylenediamine radical and n is between 2 and 5.

Mention may be made, as polyamide compounds of formula (I), of the commercial products sold by Arizona Chemical under the names Uniclear 80 and Uniclear 100 or also Uniclear 80 V, Uniclear 100 V and Uniclear 100 VG, the INCI name of which is "ethylenediamine/stearyl dimer dilinoleate copolymer". They are sold, respectively, in the form of a gel comprising 80% of active material in a mineral oil and comprising 100% of active material. They have a softening point of 88 to 94° C. These commercial products are a mixture of copolymers of a $C_{36}$ diacid condensed with ethylenediamine, with a weight-average molecular weight of approximately 6,000 g/mol. The terminal ester groups result from the esterification of the remaining acid terminators with cetyl alcohol, stearyl alcohol or their mixtures (also known as cetylstearyl alcohol).

As the silicone polyamide, mention can be made of polymers comprising at least one unit of formula (II) or (III):

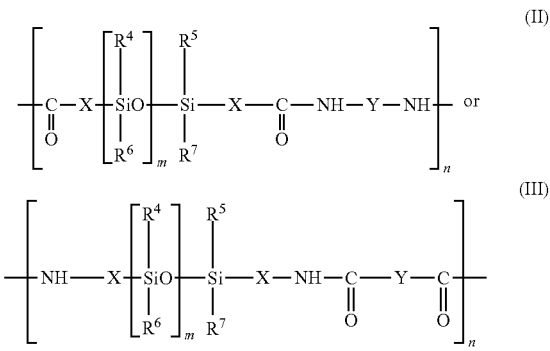

in which:
$R^4$, $R^5$, $R^6$ and $R^7$, which may be identical or different, represent a group chosen from:
  saturated or unsaturated, $C_1$ to $C_{40}$ linear, branched or cyclic hydrocarbon-based groups, which may contain in their chain one or more oxygen, sulfur and/or nitrogen atoms, and which may be partially or totally substituted with fluorine atoms,
  $C_6$ to $C_{10}$ aryl groups, optionally substituted with one or more $C_1$ to $C_4$ alkyl groups,
  polyorganosiloxane chains possibly containing one or more oxygen, sulfur and/or nitrogen atoms,
the groups X, which may be identical or different, represent a linear or branched $C_1$ to $C_{30}$ alkylenediyl group, possibly containing in its chain one or more oxygen and/or nitrogen atoms,
Y is a saturated or unsaturated $C_1$ to $C_{50}$ linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with one to three $C_1$ to $C_3$ alkyl, $C_1$ to $C_3$ hydroxyalkyl and $C_1$ to $C_6$ aminoalkyl groups, or
Y represents a group corresponding to the formula:

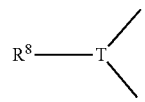

in which:
T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and
$R^8$ represents a linear or branched $C_1$-$C_{50}$ alkyl group or a polyorganosiloxane chain, possibly comprising one or more ester, amide, urethane, thiocarbamate, urea, thiourea and/or sulfonamide groups, which may possibly be linked to another chain of the polymer;
n is an integer ranging from 2 to 500 and preferably from 2 to 200, and m is an integer ranging from 1 to 1,000, preferably from 1 to 700 and better still from 6 to 200.

The amount of (b) organic lipophilic gelling agent(s) is greater than 0% by weight and less than 5% by weight relative to the total weight of the composition. The (b) organic lipophilic gelling agent(s) may be present in an amount of 0.1% by weight or more, preferably 0.2% by weight or more, more preferably 0.5% by weight or more, and most preferably 1% by weight or more, and may be present in an amount of 4.5% by weight or less, preferably 4% by weight or less, more preferably 3.5% by weight or less, and most preferably 3% by weight or less, relative to the total weight of the composition.

(Pigment Coated with Isopropyl Titanium Triisostearate)

The composition according to the present invention comprises (c) at least one pigment coated with isopropyl titanium triisostearate. Two or more (b) pigments coated with isopropyl titanium triisostearate may be used in combination. Thus, a single type of pigment coated with isopropyl titanium triisostearate or a combination of different types of pigments coated with isopropyl titanium triisostearate may be used.

The term "pigments" means white or coloured, mineral or organic particles, which are insoluble in an aqueous medium, and which are intended to colour and/or opacify the resulting composition. These pigments may be white or coloured, and mineral and/or organic.

According to a particular embodiment, the pigments used in the present invention are chosen from mineral pigments. The term "mineral pigment" means any inorganic pigment. Among the mineral pigments that are useful in the present invention, mention may be made of metal oxides, such as zirconium oxide or cerium oxide, titanium dioxide and also zinc oxide, iron oxide (black, yellow or red) or chromium oxide, as well as manganese violet, ultramarine blue, chromium hydrate and ferric blue, and metal powders, for instance aluminum powder or copper powder, or any combinations thereof. The following mineral pigments may also be used: $Ta_2O_5$, $Ti_3O_5$, $Ti_2O_3$, $TiO$, $ZrO_2$ as a mixture with $TiO_2$, $ZrO_2$, $Nb_2O_5$, $CeO_2$, or $ZnS$. In the context of the present invention, the mineral pigments are more particularly iron oxide and/or titanium dioxide.

The mean particle size of the coated pigment is in general 100 nm or more. The mean particle size of the coated pigment according to the present invention may range from 100 nm to 25 μm, preferably from 200 nm to 10 μm. For the purpose of the present invention, the D50 size, or volume average size, corresponds to the particle size defined such that 50% by volume of the particles have a size greater than D50. The volume average size may be assessed by light diffraction using a Malvern MasterSizer laser particle size analyzer, said particles to be evaluated being dispersed in a liquid medium, for instance octyldodecyl neopentanoate.

The pigments may also be nacres and/or particles with metallic glints. The term "nacres" should be understood as meaning iridescent or non-iridescent coloured particles of any shape, especially produced by certain molluscs in their shell or alternatively synthesized, which have a colour effect via optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles, at the surface of which are superposed at least two successive layers of metal oxides and/or of organic dyestuffs.

The pigments in the present invention are coated with isopropyl titanium triisostearate, i.e., the surface of the pigments is coated or treated with isopropyl titanium triisostearate.

The surface-treated pigments may be prepared according to surface treatment techniques of chemical, electronic, mechanochemical or mechanical nature that are well known to those skilled in the art. Commercial products may also be used. The surface agent of isopropyl titanium triisostearate may be absorbed, adsorbed or grafted onto the surface of the pigments by evaporation of solvent, chemical reaction and creation of a covalent bond.

According to one embodiment of the present invention, the surface treatment is constituted of a coating of the pigments. For the purposes of the present invention, the "coating" of a pigment generally denotes the total or partial surface treatment of the pigment with a surface agent, absorbed, adsorbed or grafted onto said pigment. The coating may represent from 0.1% to 20% by weight and in particular from 0.5% to 5% by weight relative to the total weight of the coated pigment.

The surface treatment with isopropyl titanium triisostearate gives the pigments a hydrophobic character. Therefore, the (c) pigment coated with isopropyl titanium triisostearate of the present invention exhibits a hydrophobic and lipophilic nature. Accordingly, the (c) pigment coated with isopropyl titanium triisostearate can be dispersed and included in the oily phase of the composition according to the present invention.

In one preferred embodiment of the present invention, the (c) pigment coated with isopropyl titanium triisostearate can be selected from titanium dioxide coated with isopropyl titanium triisostearate, iron oxide coated with isopropyl titanium triisostearate, and a combination thereof.

The (c) pigment(s) coated with isopropyl titanium triisostearate may be present in an amount of 0.1% by weight or more, preferably 1% by weight or more, more preferably 2% by weight or more, and most preferably 4% by weight or more, and may be present in an amount of 20% by weight or less, preferably 15% by weight or less, more preferably 10% by weight or less, and most preferably 8% by weight or less, relative to the total weight of the composition.

(Water)

The composition according to the present invention comprises (d) water. The (d) water forms the aqueous phase in the composition according to the present invention.

The amount of water may be 20% by weight or more, preferably 30% by weight or more, more preferably 32% by weight or more, and even more preferably 35% by weight or more, relative to the total weight of the composition.

The amount of the water may be 70% by weight or less, preferably 60% by weight or less, more preferably 50% by weight or less, and even more preferably 45% by weight or less, relative to the total weight of the composition.

(Other Ingredients)

Emulsifier

The composition according to the present invention may comprise at least one emulsifier chosen from amphoteric, anionic, cationic, or nonionic surfactants, used alone or as a mixture. Preferably, the composition comprises at least one nonionic surfactant. In particular, the emulsifier can be selected from non-ionic surfactants.

Examples of nonionic surfactants usable in the compositions of the present invention may include polyethoxylated fatty alcohols or polyglycerolated fatty alcohols, such as the adducts of ethylene oxide with lauryl alcohol, especially those containing from 9 to 50 oxyethylene units (Laureth-9 to Laureth-50 as the INCI names), in particular Laureth-9; esters of polyols and of a fatty acid possessing a saturated or unsaturated chain comprising, for example, from 8 to 24 carbon atoms, and their oxyalkylenated derivatives, that is to say, comprising oxyethylene and/or oxypropylene units, such as esters of glycerol and of a $C_8$-$C_{24}$ fatty acid, and their oxyalkylenated derivatives, in particular, polyoxyethylenated glyceryl stearate (mono-, di- and/or tristearate), for example, PEG-20 glyceryl triisostearate; monoglycerolated or polyglycerolated $C_8$-$C_{40}$ fatty esters; esters of sugar and of a $C_8$-$C_{24}$ fatty acid, such as sorbitan palmitate, sorbitan isostearate, sorbitan trioleate, and their oxyalkylenated derivatives, such as polyethoxylated sorbitol esters of $C_8$-$C_{24}$ fatty acids, in particular Polysorbate 80, such as the product marketed under the name "TWEEN 80" by Croda; ethers of sugars and of $C_8$-$C_{24}$ fatty alcohols, such as caprylyl/capryl glucoside; polyoxyethylene alkyl ethers; polyoxyethylene oxypropylene alkyl ethers; fatty acid alkanol amides; alkyl amine oxides; alkyl polyglycosides and silicone surfactants, such as polydimethylsiloxane containing oxyethylene groups and/or oxypropylene groups, for example, PEG-10 dimethicone, cetyl-PEG/PPG-10/1 dimethicone, bis-PEG/PPG-14/14 dimethicone, bis-PEG/PPG-20/20 dimethicone, PEG-9 polydimethylsiloxyethyl dimethicone, and PEG/PPG-20/6 dimethicone; and polyglyceryl fatty acid ester such as polyglyceryl-6 dicaprate, polyglyceryl-6 dioleate, polyglyceryl-6 caprylate, polyglyceryl-2 oleate, and polyglyceryl-6 polyricinoleate; and mixtures thereof.

The polyoxyethylenated fatty esters may also be selected from diesters of polyethyleneglycol and fatty acids, such as saturated or unsaturated, linear or branched, $C_8$-$C_{30}$ acids, which may have one or more substituents such as a hydroxyl group and hydroxyl groups. The fatty acids may be in the form of a polymer of fatty acids each of which has one or more hydroxyl groups. Such a polymer may be formed by the esterification of the carboxyl group of one fatty acid having one or more hydroxyl groups and the hydroxyl group of another fatty acid having one or more hydroxyl groups. Examples of such a polymer include polyhydroxystearate. Thus, as the polyoxyethylenated fatty ester, mention may be made of PEG-30 dipolyhydroxystearate.

In addition, the emulsifier can be silicone crosslinked emulsifiers, such as polyoxyalkylenated silicone elastomers and polyglycerolated silicone elastomers.

As polyoxyalkylenated silicone elastomers, use may be made of those having the following INCI names: Dimethicone/PEG-10/15 Crosspolymer, PEG-15/Lauryl Dimethicone Crosspolymer, PEG-10/Lauryl Dimethicone Crosspolymer, PEG-12 Dimethicone Crosspolymer, PEG-10 Dimethicone Crosspolymer, PEG-10 Dimethicone/Vinyl Dimethicone Crosspolymer, PEG-12 Dimethicone/PPG-20 Crosspolymer, and mixtures thereof.

As polyglycerolated silicone elastomers, mention can be made of the compounds having the following INCI names:
Dimethicone/Polyglycerin-3 Crosspolymer, Lauryl Dimethicone/Polyglycerin-3 Crosspolymer, and mixtures thereof. They are in particular sold by the company Shin Etsu under the following names: KSG-710®; INCI name Dimethicone/Polyglycerin-3 Crosspolymer and Dimethicone; KSG-810®; INCI name: Mineral Oil and Lauryl Dimethicone/Polyglycerin-3 Crosspolymer; KSG-820®; INCI name: Isododecane and Lauryl Dimethicone/Polyglycerin-3 Crosspolymer; KSG-830®; INCI name: Triethylhexanoin and Lauryl Dimethicone/Polyglycerin-3 Crosspolymer; KSG-840®; INCI name: Squalane and Lauryl Dimethicone/Polyglycerin-3 Crosspolymer.

The amount of the emulsifier(s) in the composition may be from 1% by weight or more, preferably 2% by weight or more, and more preferably 3% by weight or more, and may be 10% by weight or less, preferably 8% by weight or less, and more preferably 5% by weight or less, relative to the total weight of the composition.

Cosmetically Acceptable Hydrophilic Organic Solvent

The composition according to the present invention may comprise at least one cosmetically acceptable hydrophilic organic solvent. The cosmetically acceptable hydrophilic organic solvent(s) may include, for example, substantially linear or branched lower mono-alcohols having from 1 to 8 carbon atoms, such as ethanol, propanol, butanol, isopropanol, and isobutanol; aromatic alcohols, such as benzyl alcohol and phenylethyl alcohol; polyols or polyol ethers, such as propylene glycol, dipropylene glycol, isoprene glycol, butylene glycol, glycerine, propanediol, caprylyl glycol, sorbitol, ethylene glycol monomethyl, monoethyl and monobutyl ethers, propylene glycol ethers, such as propylene glycol monomethylether, diethylene glycol alkyl ethers, such as diethylene glycol monoethylether or monobutylether; polyethylene glycols, such as PEG-4, PEG-6, and PEG-8, and their derivatives, and a combination thereof.

The amount of the cosmetically acceptable hydrophilic organic solvent(s) in the composition according to the present invention may be from 1% by weight or more, preferably 5% by weight or more, and more preferably 10% by weight or more, and may be 25% by weight or less, preferably 20% by weight or less, and more preferably 15% by weight or less, relative to the total weight of the composition.

Organic UV Filter

The composition according to the present invention may include at least one organic UV filter. Two or more types of organic UV filters may be included in combination.

The organic UV filter may be selected from the group consisting of anthranilic derivatives; dibenzoylmethane derivatives; cinnamic derivatives, such as ethylhexyl methoxycinnamate; salicylic derivatives such as homosalate (homomenthyl salicylate) and ethylhexyl salicylate; camphor derivatives; benzophenone derivatives; β,β-diphenylacrylate derivatives; triazine derivatives; benzotriazole derivatives; benzalmalonate derivatives; benzimidazole derivatives; imidazoline derivatives; bis-benzoazolyl derivatives; p-aminobenzoic acid (PABA) and derivatives thereof; benzoxazole derivatives; screening polymers and screening silicones; dimers derived from α-alkylstyrene; 4,4-diarylbutadienes; octocrylene and derivatives thereof, guaiazulene and derivatives thereof, rutin and derivatives thereof, flavonoids, biflavonoids, oryzanol and derivatives thereof, quinic acid and derivatives thereof, phenols, retinol, cysteine, aromatic amino acids, peptides having an aromatic amino acid residue, and mixtures thereof.

The amount of the organic UV filter(s) in the composition may be from 0.1% by weight or more, preferably 1% by weight or more, and more preferably 3% by weight or more, and 15% by weight or less, preferably 10% by weight or less, and more preferably 7% by weight, relative to the total weight of the composition.

Inorganic UV Filter

The composition according to the present invention may comprise at least one inorganic UV filter. Two or more types of inorganic UV filters may be included in combination.

It is preferable that the inorganic UV filter be in the form of a fine particle such that the mean (primary) particle diameter thereof ranges from 1 nm to 50 nm, preferably 5 nm to 40 nm, and more preferably 10 nm to 30 nm. The mean (primary) particle size or mean (primary) particle diameter here is an arithmetic mean diameter.

The inorganic UV filter can be selected from the group consisting of metal oxides which may or may not be coated, and mixtures thereof.

Preferably, the inorganic UV filters may be selected from metal oxides (mean size of the primary particles: generally from 5 nm to 50 nm, preferably from 10 nm to 50 nm), such as, for example, titanium oxide (amorphous or crystalline in the rutile and/or anatase form), iron oxide, zinc oxide, zirconium oxide or cerium oxide, which are all UV photoprotective agents that are well known per se. Preferably, the inorganic UV filters may be selected from titanium oxide, zinc oxide, and more preferably titanium oxide.

The inorganic UV filter may or may not be coated. The inorganic UV filter may have at least one coating. The coating may comprise at least one compound selected from the group consisting of alumina, silica, aluminum hydroxide, silicones, slimes, fatty acids or salts thereof (such as sodium, potassium, zinc, iron, or aluminum salts), fatty alcohols, lecithin, amino acids, polysaccharides, proteins, alkanolamines, waxes such as beeswax, (meth)acrylic polymers, organic UV filters, and (per)fluoro compounds.

The coated inorganic UV filters may be titanium oxides coated with:

silica, such as the product "Sunveil" from Ikeda;

silica and iron oxide, such as the product "Sunveil F" from Ikeda;

silica and alumina, such as the products "Microtitanium Dioxide MT 500 SA" from Tayca, "Tioveil" from Tioxide, and "Mirasun TiW 60" from Rhodia;

alumina, such as the products "Tipaque TTO-55 (B)" and "Tipaque TTO-55 (A)" from Ishihara, and "UVT 14/4" from Kemira;

alumina and aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck;

alumina and aluminum laurate, such as the product "Microtitanium Dioxide MT 100 S" from Tayca;

iron oxide and iron stearate, such as the product "Microtitanium Dioxide MT 100 F" from Tayca;

zinc oxide and zinc stearate, such as the product "BR351" from Tayca;

silica and alumina and treated with a silicone, such as the products "Microtitanium Dioxide MT 600 SAS", "Microtitanium Dioxide MT 500 SAS", and "Microtitanium Dioxide MT 100 SAS" from Tayca;

silica, alumina, and aluminum stearate and treated with a silicone, such as the product "STT-30-DS" from Titan Kogyo;

silica and treated with a silicone, such as the product "UV-Titan X 195" from Kemira;

alumina and treated with a silicone, such as the products "Tipaque TTO-55 (S)" from Ishihara or "UV Titan M 262" from Kemira;

triethanolamine, such as the product "STT-65-S" from Titan Kogyo;

stearic acid, such as the product "Tipaque TTO-55 (C)" from Ishihara; or sodium hexametaphosphate, such as the product "Microtitanium Dioxide MT 150 W" from Tayca;

stearic acid and aluminum hydroxide, such as the product "MT-100 TV" from Tayca, with a mean primary particle diameter of 15 nm;

dimethicone and stearic acid and aluminum hydroxide, such as the product "SA-TTO-S4" from Miyoshi Kasei, with a mean primary particle diameter of 15 nm;

silica, such as the product "MT-100 WP" from Tayca, with a mean primary particle diameter of 15 nm;

dimethicone and silica and aluminum hydroxide, such as the products "MT-Y02" and "MT-Y-110 M3 S" from Tayca, with a mean primary particle diameter of 10 nm;

dimethicone and aluminum hydroxide, such as the product "SA-TTO-S3" from Miyoshi Kasei, with a mean primary particle diameter of 15 nm;

dimethicone and alumina, such as the product "UV TITAN M170" from Sachtleben, with a mean primary particle diameter of 15 nm;

silica and aluminum hydroxide and alginic acid, such as the product "MT-100 AQ" from Tayca, with a mean primary particle diameter of 15 nm; and aluminum hydroxide and dimethicone and hydrogen dimethicone, such as "SAS-UT-A30" from Miyoshi Kasei.

The amount of the inorganic UV filter(s) in the composition may be from 0.1% by weight or more, preferably 1% by weight or more, and more preferably 3% by weight or more, and 15% by weight or less, preferably 10% by weight or less, and more preferably 7% by weight, relative to the total weight of the composition.

Silicone Elastomer

The composition according to the present invention may comprise at least one silicone elastomer. Two or more types of silicone elastomers may be included in combination.

The term "silicone elastomer" or "organopolysiloxane elastomer" here is intended to mean a supple, deformable silicone with viscoelastic properties and in particular with the consistency of a sponge or a supple sphere. The silicone elastomer can particularly be a crosslinked silicone elastomer.

The silicone elastomer is advantageously a non-emulsifying elastomer. The term "non-emulsifying" here defines silicone elastomers not containing a hydrophilic chain and in particular not containing polyoxyalkylene units (in particular polyoxyethylene or polyoxypropylene units) or a polyglyceryl unit. Thus, according to a specific form of the present invention, the composition comprises a silicone elastomer devoid of polyoxyalkylene units and of polyglyceryl unit.

In particular, the silicone elastomer used in the present invention is chosen from Dimethicone Crosspolymer (INCI name), Vinyl Dimethicone Crosspolymer (INCI name), Dimethicone/Vinyl Dimethicone Crosspolymer (INCI name) or Dimethicone Crosspolymer-3 (INCI name).

According to a particular embodiment of the present invention, use is made of a gel of silicone elastomer dispersed in a silicone oil chosen from a non-exhaustive list comprising cyclopentadimethylsiloxane, dimethicones, dimethylsiloxanes, methyl trimethicone, phenyl methicone, phenyl dimethicone, phenyl trimethicone and cyclomethicone, preferably a linear silicone oil chosen from polydimethylsiloxanes (PDMSs) or dimethicones with a viscosity at 25° C. ranging from 1 to 500 cSt, optionally modified with optionally fluorinated aliphatic groups, or with functional groups such as hydroxyl, thiol and/or amine groups.

Mention may be made in particular of the compounds having the following INCI names:

Dimethicone/Vinyl Dimethicone Crosspolymer, such as USG-105 and USG-107A from the company Shin-Etsu; DC9506 and DC9701 from the company Dow Corning;

Dimethicone/Vinyl Dimethicone Crosspolymer (and) Dimethicone, such as KSG-6 and KSG-16 from the company Shin-Etsu;

Dimethicone/Vinyl Dimethicone Crosspolymer (and) Cyclopentasiloxane, such as KSG-15;

Cyclopentasiloxane (and) Dimethicone Crosspolymer, such as DC9040, DC9045 and DC5930 from the company Dow Corning;

Dimethicone (and) Dimethicone Crosspolymer, such as DC9041 from the company Dow Corning;

Dimethicone (and) Dimethicone Crosspolymer, such as Dow Corning EL-9240® Silicone Elastomer Blend from the company Dow Corning (mixture of polydimethylsiloxane crosslinked with hexadiene/polydimethylsiloxane (2 cSt));

$C_{4-24}$ Alkyl Dimethicone/Divinyl Dimethicone Crosspolymer, such as NuLastic Silk MA by the company Alzo;

Polysilicone-11 and Cyclohexasiloxane such as Gransil RPS-D6® from the company Grant Industries (comprising 87% of Cyclohexasiloxane and 13% of Polysilicone-11), Polysilicone-11 and isododecane such as Gransil PC-12® from the company Grant Industries (with a polysilicone-11:isododecane weight ratio of 13:87).

The amount of the silicone elastomer(s) in the composition may be 0.1% by weight or more, preferably 0.5% by weight or more, and more preferably 1% by weight or more, and 10% by weight or less, preferably 7% by weight or less, and more preferably 5% by weight or less, relative to the total weight of the composition.

Hydrophilic Gelling Agent

The composition according to the present invention may comprise at least one hydrophilic gelling agent. Two or more types of hydrophilic gelling agents may be included in combination.

The term "hydrophilic" here means substances having a solubility of at least 1 g/L, preferably at least 10 g/L, and more preferably at least 100 g/L, in water at room temperature (25° C.) and atmospheric pressure ($10^5$ Pa). Preferably, the hydrophilic gelling agent is insoluble in oil, i.e., have a solubility of less than 1 g/L, preferably of less than 0.1 g/L in oils at room temperature (25° C.) and atmospheric pressure ($10^5$ Pa).

The hydrophilic gelling agent usable in the composition according to the present invention may include water soluble polymers such as, for example, anionic acrylate polymers such as Salcare® AST and cationic acrylate polymers such as Salcare® SC96; acrylamidopropyltrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28; glyceryl polymethacrylate, Acrylates/Steareth-20 Methacrylate Copolymer; bentonite; gums such as cellulose gum, alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based gelling agents, sodium carbomer, and mixtures thereof.

The amount of the hydrophilic gelling agent(s) in the composition may be 0.05% by weight or more, preferably 0.1% by weight or more, and more preferably 0.2% by weight or more, and 5% by weight or less, preferably 3% by weight or less, and more preferably 2% by weight or less, relative to the total weight of the composition.

In one preferred embodiment of the present invention, the composition comprise at least one hydrophilic gelling agent selected from water soluble polysaccharides, preferably glycosaminoglycans and their salts, and their derivatives. In one more preferred embodiment of the present invention, the composition comprises at least one hydrophilic gelling agent selected from hyaluronic acid and their salts, and their derivatives, such as sodium hyaluronate and acetylated sodium hyaluronate, and mixtures thereof.

Therefore, the present invention also relates to a composition in the form of a water-in-oil (W/O) emulsion comprising an oily phase and an aqueous phase, comprising:
(a) at least one oil;
(b) at least one organic lipophilic gelling agent;
(c) at least one pigment coated with isopropyl titanium triisostearate;
(d) water; and
(e) at least one hydrophilic gelling agent selected from glycosaminoglycans and their salts, and their derivatives, preferably hyaluronic acid and their salts, and their derivatives, such as sodium hyaluronate and acetylated sodium hyaluronate, and mixtures thereof,
wherein
the amount of the (b) lipophilic gelling agent is greater than 0% by weight and less than 5% by weight relative to the total weight of the composition, and
the amount of the aqueous phase is at least 50% by weight relative to the total weight of the composition.

In this embodiment, the (b) organic lipophilic gelling agent is preferably chosen from polysaccharide fatty acid esters, semi-crystalline polymers, polyamides, and mixtures thereof, more preferably polysaccharide fatty acid esters, and in particular dextrin esters.

Accordingly, in a specific embodiment of the present invention, the composition comprises (b) at least one organic lipophilic gelling agent selected from dextrin esters; and (e) at least one hydrophilic gelling agent selected from glycosaminoglycans and their salts, and their derivatives, in particular selected from hyaluronic acid and their salts, and their derivatives, such as sodium hyaluronate and acetylated sodium hyaluronate, and mixtures thereof.

In one preferred embodiment of the present invention, the amount of hydrophilic gelling agent selected from glycosaminoglycans and their salts, and their derivatives in the composition may be 0.1% by weight or more, preferably 0.2% by weight or more, more preferably 0.5% by weight or more, and in particular 0.7% by weight or more, and may be 5% by weight or less, preferably 4% by weight or less, and more preferably 3% by weight or less, relative to the total weight of the composition.

Adjuvants

The compositions according to the present invention may also contain various adjuvants conventionally used in compositions for cosmetic products, which may be selected from a physiologically acceptable medium, cationic, anionic, nonionic, amphoteric or zwitterionic polymers or mixtures thereof, organic fillers, antioxidants, such as tocopherol, basifying agents, such as ethanol amine, acidifying agents, neutralizing agents, such as triethanolamine, sequestering agents, such as disodium EDTA, plant extracts, such as *Rosa centifolia* flower extract, fragrances, emollients, dispersing agents, dyes, film-forming agents and/or thickeners, ceramides, preservatives, such as phenoxy ethanol and chlorphenesin, electrolytes, such as magnesium sulfate, co-preservatives, such as decylene glycol, ethylhexyl glycerin, and caprylyl glycol, and opacifying agents.

The amount of the additional ingredient(s) is not limited, but may be from 0.1 to 30% by weight relative to the total weight of the composition according to the present invention.

The composition preferably exhibits a pH which is compatible with the skin and which generally ranges from 3 to 9 and preferably from 4 to 8.

The viscosity of the composition according to the present invention is not particularly limited. The viscosity can be measured at 25° C. with viscosimeters or rheometers preferably with cone-plate or parallel-plate geometry. Preferably, the viscosity of the composition can range, for example, from 1 to 5000 Pa·s at 25° C. and 21 s$^{-1}$. In addition, the composition may possess a Newtonian nature.

The composition according to the present invention can be manufactured by mixing the (a) at least one oil, (b) at least one organic lipophilic gelling agent, (c) at least one pigment coated with isopropyl titanium triisostearate, and (d) water, as well as one or more optional ingredients as mentioned above.

[Cosmetic Process]

The present invention also relates to a cosmetic process for a keratin substrate, such as skin, comprising applying to the keratin substrate the composition according to the present invention.

The composition according to the present invention may be intended for application onto a keratin substance such as skin, for example, of the face, neck and body, to make an attractive appearance, to conceal imperfections, such as blemishes, wrinkles, pores. The composition is generally applied on a keratin substance, such as skin, with the hands or an applicator, for example, a sponge applicator.

The composition according to the present invention can be used in the topical skin care composition in the form of a lotion, a milky lotion, a cream, a liquid gel, a paste, a serum, or a spray.

The cosmetic process is preferably intended for making up and/or caring for skin, preferably facial skin. The composition used according to the present invention is preferably intended to be used as a leave-in type cosmetic composition. The term "leave-in" means a composition that is not intended to be washed out or removed immediately after application.

Preferably, the composition according to the present invention can be used as a liquid foundation, a make-up base, and skin care cream composition, and in particular a liquid foundation. Therefore, the present invention also relates to a use of the composition according to the present invention as a make-up active in a cosmetic liquid composition, such as a liquid foundation, a make-up base, and skin care cream.

EXAMPLES

The present invention will be described in a more detailed manner by way of examples. However, these examples should not be construed as limiting the scope of the present invention.

Example 1 and Comparative Examples 1 to 6

The following compositions according to Example 1 and Comparative Examples 1 to 6, shown in Table 1, were prepared as follows. First, an aqueous phase was prepared by mixing and dissolving all the ingredients listed in "Aqueous Phase" in Table 1 below at 45° C. until the mixture became homogenous. The aqueous mixture was then cooled to room temperature. An oily phase was prepared by mixing all the ingredients listed in "Oily Phase" in Table 1 at 90° C. for 10 minutes. The pigments and silicone elastomer were added to the oily mixture obtained and were dispersed well. The oily mixture was cooled to room temperature and then the aqueous mixture was added to the oily mixture. The obtained mixture was emulsified for 10 minutes at 3,000 rpm with a homogenizer to obtain a W/O emulsion composition.

The numerical values for the amounts of the ingredients in Table 1 are all based on "% by weight" as active raw materials.

TABLE 1

| | Ingredients | Ex. 1 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|
| Oily Phase | PEG-9 Polydimethylsiloxyethyl Dimethicone | 0.5 | 0.5 | 0.5 | 0.5 | 0.5 | 0.5 | 0.5 |
| | PEG-30 Dipolyhydroxystearate | 0.5 | 0.5 | 0.5 | 0.5 | 0.5 | 0.5 | 0.5 |
| | Cetyl PEG/PPG-10/1 Dimethicone | 2.5 | 2.5 | 2.5 | 2.5 | 2.5 | 2.5 | 2.5 |
| | Sorbitan Isostearate | 0.3 | 0.3 | 0.3 | 0.3 | 0.3 | 0.3 | 0.3 |
| | Cetyl Ethylhexanoate | 2.6 | 2.6 | 2.6 | 2.6 | 2.6 | 2.6 | 2.6 |
| | Diphenylsiloxy Phenyl Trimethicone | 5 | 5 | 5 | 5 | 5 | 5 | 5 |
| | Ethylhexyl Salicylate | 2.5 | 2.5 | 2.5 | 2.5 | 2.5 | 2.5 | 2.5 |
| | Homosalate | 2.5 | 2.5 | 2.5 | 2.5 | 2.5 | 2.5 | 2.5 |
| | Dimethicone | QSP100 | QSP100 | QSP100 | QSP100 | QSP100 | QSP100 | QSP100 |
| | Isohexadecane | 7 | 7 | 7 | 7 | 7 | 7 | 7 |
| | Dextrin Palmitate | 2 | 2 | 2 | 0 | 5 | 2 | 2 |
| | Dimethicone (and) Dimethicone/Vinyl Dimethicone Crosspolymer | 2 | 2 | 2 | 2 | 2 | 2 | 2 |
| Powder | Titanium Dioxide (and) Aluminum Hydroxide (and) Dimethicone (and) Hydrogen Dimethicone | 5 | 5 | 5 | 5 | 5 | 5 | 5 |
| | Titanium Dioxide (and) Alumina (and) Isopropyl Titanium Triisostearate | 4.9 | — | — | 4.9 | 4.9 | 4.9 | 4.9 |
| | Iron Oxides (and) Isopropyl Titanium Triisostearate | 0.6 | — | — | 0.6 | 0.6 | 0.6 | 0.6 |
| | Titanium Dioxide | — | 4.9 | — | — | — | — | — |
| | Iron Oxide | — | 0.6 | — | — | — | — | — |
| | Titanium Dioxide (and) Disodium Stearoyl Glutamate (and) Aluminum Hydroxide | — | — | 4.9 | — | — | — | — |
| | Iron Oxide (and) Disodium Stearoyl Glutamate (and) Aluminum Hydroxide | — | — | 0.6 | — | — | — | — |

TABLE 1-continued

| | Ingredients | Ex. 1 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|
| Aqueous Phase | Water | 38 | 38 | 38 | 38 | 38 | 25 | 30 |
| | Magnesium Sulfate | 0.7 | 0.7 | 0.7 | 0.7 | 0.7 | 0.7 | 0.7 |
| | Chlorphenesin | 0.2 | 0.2 | 0.2 | 0.2 | 0.2 | 0.2 | 0.2 |
| | Glycerin | 5.7 | 5.7 | 5.7 | 5.7 | 5.7 | 5.7 | 5.7 |
| | Phenoxyethanol | 0.7 | 0.7 | 0.7 | 0.7 | 0.7 | 0.7 | 0.7 |
| | Caprylyl Glycol | 0.5 | 0.5 | 0.5 | 0.5 | 0.5 | 0.5 | 0.5 |
| | Butylene Glycol | 8 | 8 | 8 | 8 | 8 | 8 | 8 |
| | Cellulose Gum | 0.5 | 0.5 | 0.5 | 0.5 | 0.5 | 0.5 | 0.5 |

[Evaluation]

The compositions according to Example 1 and Comparative Examples 1 to 6 were evaluated in the following aspects.

(Sensory Test)

Each of the compositions according to Example 1 and Comparative Examples 1 to 6 was applied to the faces of 5 panelists and the fresh and moisture sensation as well as coverage efficacy were evaluated. Each of the compositions was applied on the panelists' faces by the panelists themselves and the panelists evaluated with respect to a fresh and moist sensation as well as coverage efficacy by scoring: 1 (very bad) to 5 (very good). The average of the scores was calculated and was categorized in accordance with the following criteria.

Good≥4
4>Poor≥3
3>Very Poor (Stability)

Each compositions according to Example 1 and Comparative Examples 1 to 6 were left for two months at 45° C., and the appearance of each composition was then visually observed and categorized in accordance with the following criteria.

Good: no separation
Poor: the oily phase separated slightly
Very Poor: the oily phase separated The results of these evaluations are shown in Table 2 below.

TABLE 2

| Evaluation | Ex. 1 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|
| Freshness | Good | Good | Good | Good | Very Poor | Very Poor | Poor |
| Coverage | Good | Very Poor | Very Poor | Good | Good | Poor | Good |
| Stability | Good | Very Poor | Very Poor | Very Poor | Good | Good | Good |

The composition according to Example 1 was able to provide keratinous substances, such as skin, with an improved fresh and moist feeling as well as a coverage effect, while it maintained stable.

On the other hand, the compositions according to Comparative Examples 1 and 2, which did not include a pigment coated with isopropyl titanium triisostearate, exhibited a very poor coverage efficacy. In addition, the composition according to Comparative Example 1, which includes a non-coated pigment instead of a pigment coated with isopropyl titanium triisostearate of the present invention, exhibited very poor stability.

The composition according to Comparative Example 3, which did not include the organic lipophilic gelling agent, exhibited very poor stability, while the composition according to Comparative Example 4, which included the organic lipophilic gelling agent in an amount of 5% by weight of the composition, provided a very poor freshness sensation.

The composition according to Comparative Example 5, which includes 25% by weight of an aqueous phase, provided a very poor freshness sensation and a poor coverage efficacy. The composition according to Comparative Example 6, which included even 30% by weight of an aqueous phase, provided a poor freshness sensation.

Examples 2 to 6

The following compositions according to Examples 2 to 6, shown in Table 3, were prepared as follows. First, an aqueous phase was prepared by mixing and dissolving all the ingredients listed in "Aqueous Phase" in Table 3 below at 45° C. until the mixture became homogenous. The aqueous mixture was then cooled to room temperature. An oily phase was prepared by mixing all the ingredients listed in "Oily Phase" in Table 3 at 90° C. for 10 minutes. The pigments and silicone elastomer were added to the oily mixture obtained and were dispersed well. The oily mixture was cooled to room temperature and then the aqueous mixture was added to the oily mixture. The obtained mixture was emulsified for 10 minutes at 3,000 rpm with a homogenizer to obtain a W/O emulsion composition.

The numerical values for the amounts of the ingredients in Table 3 are all based on "% by weight" as active raw materials.

TABLE 3

| | Ingredients | Ex. 2 | Ex. 3 | Ex. 4 | Ex. 5 | Ex. 6 |
|---|---|---|---|---|---|---|
| Oily Phase | PEG-9 Polydimethylsiloxyethyl Dimethicone | 0.5 | 0.5 | 0.5 | 0.5 | 0.5 |
| | PEG-30 Dipolyhydroxystearate | 0.5 | 0.5 | 0.5 | 0.5 | 0.5 |
| | Cetyl PEG/PPG-10/1 Dimethicone | 2.5 | 2.5 | 2.5 | 2.5 | 2.5 |
| | Sorbitan Isostearate | 0.3 | 0.3 | 0.3 | 0.3 | 0.3 |
| | Cetyl Ethylhexanoate | 2.6 | 2.6 | 2.6 | 2.6 | 2.6 |

TABLE 3-continued

| | Ingredients | Ex. 2 | Ex. 3 | Ex. 4 | Ex. 5 | Ex. 6 |
|---|---|---|---|---|---|---|
| | Diphenylsiloxy Phenyl Trimethicone | 5 | 5 | 5 | 5 | 5 |
| | Ethylhexyl Salicylate | 2.5 | 2.5 | 2.5 | 2.5 | 2.5 |
| | Homosalate | 2.5 | 2.5 | 2.5 | 2.5 | 2.5 |
| | Dimethicone | QSP100 | QSP100 | QSP100 | QSP100 | QSP100 |
| | Isohexadecane | 7 | 7 | 7 | 7 | 7 |
| | Dextrin Palmitate | 2 | 2 | 2 | 2 | 2 |
| | Dimethicone (and) Dimethicone/Vinyl Dimethicone Crosspolymer | 2 | 2 | 2 | 2 | 2 |
| Powder | Titanium Dioxide (and) Aluminum Hydroxide (and) Dimethicone (and) Hydrogen Dimethicone | 5 | 5 | 5 | 5 | 5 |
| | Titanium Dioxide (and) Alumina (and) Isopropyl Titanium Triisostearate | 4.9 | 4.9 | 4.9 | 4.9 | 4.9 |
| | Iron Oxides (and) Isopropyl Titanium Triisostearate | 0.6 | 0.6 | 0.6 | 0.6 | 0.6 |
| Aqueous Phase | Water | 37 | 37 | 37.5 | 37.5 | 37.5 |
| | Magnesium Sulfate | 0.7 | 0.7 | 0.7 | 0.7 | 0.7 |
| | Chlorphenesin | 0.2 | 0.2 | 0.2 | 0.2 | 0.2 |
| | Glycerin | 5.7 | 5.7 | 5.7 | 5.7 | 5.7 |
| | Phenoxyethanol | 0.7 | 0.7 | 0.7 | 0.7 | 0.7 |
| | Caprylyl Glycol | 0.5 | 0.5 | 0.5 | 0.5 | 0.5 |
| | Butylene Glycol | 8 | 8 | 8 | 8 | 8 |
| | Cellulose Gum | 0.5 | 0.5 | 0.5 | 0.5 | 0.5 |
| | Sodium Hyaluronate | 2 | 3 | — | — | — |
| | Acetylated Sodium Hyaluronate | — | — | 1 | 2 | 3 |

[Evaluation]

The compositions according to Examples 2 to 6 were evaluated in the following aspects.

(Sensory Test)

Each of the compositions according to Examples 2 to 6 was applied to the faces of 5 panelists and the fresh and moisture sensation as well as coverage efficacy were evaluated. Each of the compositions was applied on the panelists' faces by the panelists themselves and the panelists evaluated with respect to a fresh and moist sensation as well as coverage efficacy by scoring: 1 (very bad) to 5 (very good). The average of the scores was calculated and was categorized in accordance with the following criteria.

Very Good≥4.5
Good≥4
4>Poor≥3
3>Very Poor (Stability)

Each compositions according to Examples 2 to 6 were left for two months at 45° C., and the appearance of each composition was then visually observed and categorized in accordance with the following criteria.

Very Good: no separation and no viscosity reduction
Good: no separation
Poor: the oily phase separated slightly
Very Poor: the oily phase separated The results of these evaluations are shown in Table 4 below.

TABLE 4

| Evaluation | Ex. 2 | Ex. 3 | Ex. 4 | Ex. 5 | Ex. 6 |
|---|---|---|---|---|---|
| Freshness | Good | Good | Good | Good | Good |
| Coverage | Very Good | Very Good | Very Good | Very Good | Very Good |
| Stability | Very Good | Very Good | Very Good | Very Good | Very Good |

The compositions according to Examples 2 to 6, which include sodium hyaluronate or acetylated sodium hyaluronate in addition to the formulation of Example 1, were also able to provide keratinous substances, such as skin, with an improved fresh and moist feeling as well as a coverage effect, while it maintained stable. In particular, these compositions exhibited a very good stability property and a very good coverage property.

Therefore, it can be concluded that the composition according to the present invention has a great benefit since it can provide excellent cosmetic properties, such as providing a fresh and moist feeling as well as a good covering property while it remains stable. Therefore the compositions according to the present invention are very useful as cosmetic liquid compositions.

The invention claimed is:

1. A composition in the form of a water-in-oil (W/O) emulsion comprising an oily phase and an aqueous phase, comprising:
   (a) at least one oil;
   (b) at least one organic lipophilic gelling agent;
   (c) at least one pigment coated with isopropyl titanium triisostearate;
   (d) water; and
   (e) at least one hydrophilic gelling agent selected from water soluble polysaccharides in an amount of 0.05% by weight or more and 5% by weight or less relative to the total weight of the composition,
   wherein the amount of the (b) lipophilic gelling agent is greater than 0% by weight and less than 5% by weight relative to the total weight of the composition, and
   the amount of the aqueous phase is at least 50% by weight relative to the total weight of the composition.

2. The composition according to claim 1, wherein the (b) organic lipophilic gelling agent is chosen from polysaccharide fatty acid esters, semi-crystalline polymers, polyamides, and mixtures thereof.

3. The composition according to claim 1, wherein the (b) organic lipophilic gelling agent is chosen from polysaccharide fatty acid esters.

4. The composition according to claim 3, wherein the polysaccharide fatty acid esters are dextrin esters.

5. The composition according to claim 1, wherein the pigment of the (c) pigment coated with isopropyl titanium triisostearate is chosen from metal oxides and mixtures thereof.

6. The composition according to claim 1, wherein the amount of the (c) pigment (s) coated with isopropyl titanium triisostearate is 0.1% by weight or more and is 20% by weight or less relative to the total weight of the composition.

7. The composition according to claim 1, wherein the amount of the aqueous phase is 90% by weight or less relative to the total weight of the composition.

8. The composition according to claim 1, wherein the amount of the (a) oil is 5% by weight or more and is 45% by weight or less relative to the total weight of the composition.

9. The composition according to claim 1, wherein the amount of the (d) water is 20% by weight or more and is 70% by weight or less relative to the total weight of the composition.

10. The composition according to claim 1, further comprising at least one organic UV filter.

11. The composition according to claim 1, wherein the amount of the oil phase is 5% by weight or more and is 49% by weight or less relative to the total weight of the composition.

12. A cosmetic process for a keratin substance, comprising:
applying onto the keratin substance the composition according to claim 1.

13. A composition in the form of a water-in-oil (W/O) emulsion comprising an oily phase and an aqueous phase, comprising:
(a) at least one oil;
(b) at least one organic lipophilic gelling agent;
(c) at least one pigment coated with isopropyl 1 titanium triisostearate;
(d) water; and
(e) at least one hydrophilic gelling agent selected from glycosaminoglycans and their salts, and their derivatives, and mixtures thereof in an amount of 0.05% by weight or more and 5% by weight or less relative to the total weight of the composition,
wherein the amount of the (b) lipophilic gelling agent is greater than 0% by weight and less than 5% by weight relative to the total weight of the composition, and
the amount of the aqueous phase is at least 50% by weight relative to the total weight of the composition.

14. The composition according to claim 13, wherein the (b) organic lipophilic gelling agent is dextrin esters.

* * * * *